United States Patent [19]

Dussaud et al.

[11] 4,410,326
[45] Oct. 18, 1983

[54] ADHESIVE-TYPE SECURING DEVICE FOR DISPOSABLE DIAPERS, AND DISPOSABLE DIAPER COMPRISING SUCH A SECURING DEVICE

[75] Inventors: Jacques Dussaud, Lille; Raphael De Jonckheere, Bondues, both of France

[73] Assignee: Boussac Saint Freres B.S.F., Lille, France

[21] Appl. No.: 304,440

[22] Filed: Sep. 21, 1981

[30] Foreign Application Priority Data

Sep. 23, 1980 [FR] France .................. 80 20442

[51] Int. Cl.³ ............................................ A41B 13/02
[52] U.S. Cl. .................................................. 604/390
[58] Field of Search ............... 128/284, 287, DIG. 30; 604/389–390

[56] References Cited

U.S. PATENT DOCUMENTS

| | | |
|---|---|---|
| 3,869,761 | 3/1975 | Schaar . |
| 3,983,876 | 10/1976 | Cepuritis ................ 128/DIG. 30 |
| 3,989,048 | 11/1976 | Cepuritis et al. . |
| 3,990,449 | 11/1976 | Cheslow ................ 128/DIG. 30 |
| 3,995,639 | 12/1976 | Cheslow . |
| 3,999,546 | 12/1976 | Feldman et al. . |
| 4,010,754 | 3/1977 | Pieniak ................ 128/DIG. 30 |
| 4,014,339 | 3/1977 | Tritsch . |
| 4,034,752 | 7/1977 | Tritsch . |
| 4,069,821 | 1/1978 | Fitzgerald et al. ......... 128/DIG. 30 |
| 4,090,516 | 5/1978 | Schaar . |
| 4,178,933 | 12/1979 | Nemeth ................ 128/DIG. 30 |
| 4,209,016 | 6/1980 | Schaar ................ 128/DIG. 30 |

FOREIGN PATENT DOCUMENTS 2078794 11/1971 France .
2259553 8/1975 France .

*Primary Examiner*—C. Fred Rosenbaum
*Attorney, Agent, or Firm*—Millen & White

[57] ABSTRACT

Improved adhesive-type securing device, notably for disposable diapers, and disposable diaper comprising such a securing device.

Adhesive-type securing device, notably for disposable diapers comprising an impermeable thin flexible sheet carrying absorbent padding.

Each of the diaper securing devices (7) comprises two tearable adhesive tabs (8, 9) fixed to the back part (4) of the diaper and capable of being fixed separately onto the thin sheet (1) of the front part of the diaper.

Application: notably to disposable diapers for infants.

6 Claims, 3 Drawing Figures

ADHESIVE-TYPE SECURING DEVICE FOR DISPOSABLE DIAPERS, AND DISPOSABLE DIAPER COMPRISING SUCH A SECURING DEVICE

BACKGROUND OF THE INVENTION

The present invention relates to an improved adhesive-type securing device, especially adapted for use on disposable diapers for infants, and also to a disposable diaper comprising such a securing device.

Adhesive-type securing devices for diapers are well known (see, for example, U.S. Pat. Nos. 3,180,355; 3,630,201; 4,047,530; 4,049,001; 4,050,463; and French Pat. No. 74 36 169). These securing devices generally consist of an adhesive tab fixed to one part of the diaper which is then being fixed to another part of the diaper in order to close the diaper at the level of the infant's waist.

The disposable diapers consist of an envelope made up of a thin flexible sheet which is impermeable and has absorbent padding on one side. The adhesive tab is fixed to one part of this sheet, i.e., to the part forming the back of the diaper, and is then secured, when the diaper is being closed, to another part of this same sheet, i.e., to the part forming the front of the disposable diaper.

It often happens that one may wish to reopen and reclose the diaper that has been secured in this way, for example, to check whether the infant has yet wet the absorbent pad or to correct the diaper's fit, for example, in order to tighten it round the waist. And it often turns out that by thus trying to open a disposable diaper in which the said sheet is very thin generally causes either the adhesive tab to be torn from the back part of the diaper, or the front sheet area to which the adhesive tab adheres and is torn, with this ripped off area remaining stuck to the adhesive tab. In either case it is no longer possible to reclose the diaper which is thus unserviceable, although the absorbent padding may not yet be wet.

Similar securing devices are used for other applications as well, for example the widest variety of envelopes and packagings made of thin materials, and in these cases also include the same problems, i.e., that once the device is opend it is generally destroyed, preventing any reuse, although this might be advantageous in certain cases.

SUMMARY OF THE INVENTION

The object of this invention is to provide an adhesive securing device of this type, which allows, after a first securement, at least one opening operation followed by a second securement or closure.

The securing device according to the invention comprises at least two tearable adhesive tabs fixed to one part of a thin sheet acting as an envelope; these tabs can be attached separately by adhesive onto another part of the said sheet.

It is thus possible to use one of the two adhesive tabs for the first closing of the envelope. In order to reopen the envelope the said tab is torn through, which causes no damage to the envelope. In order to reclose the envelope subsequently the second adhesive tab is then used. This second tab can be fixed with no problem to the other part of the envelope which has not been torn during the previous opening operation.

According to a particularly simple embodiment of the securing device according to the invention, the two adhesive tabs consist of a single tab, of increased width, fixed to part of the envelope, with only the section of the tab designed to be secured to the other part of the envelope being divided into two parts or tabs placed side by side. The advantage of this embodiment resides in the fact that the manufacture and installation of these double adhesive tabs starting with adhesive tape can be performed on the machines already used for the single tabs. The only modification required consists of increasing the width of the adhesive tape from which the tabs are formed and in providing a station for cutting the tabs along part of their length.

Another object of the invention is to provide a disposable diaper, notably for infants, comprising one or more securing devices which can be reused in case of need.

BRIEF DESCRIPTION OF THE DRAWINGS

With reference to the appended drawings, an illustrative embodiment which is in no way limiting of a securing device according to the invention will be described below in greater detail in its application to a disposable diaper; in these drawings.

DETAILED DISCUSSION OF THE INVENTION

Figure 1:
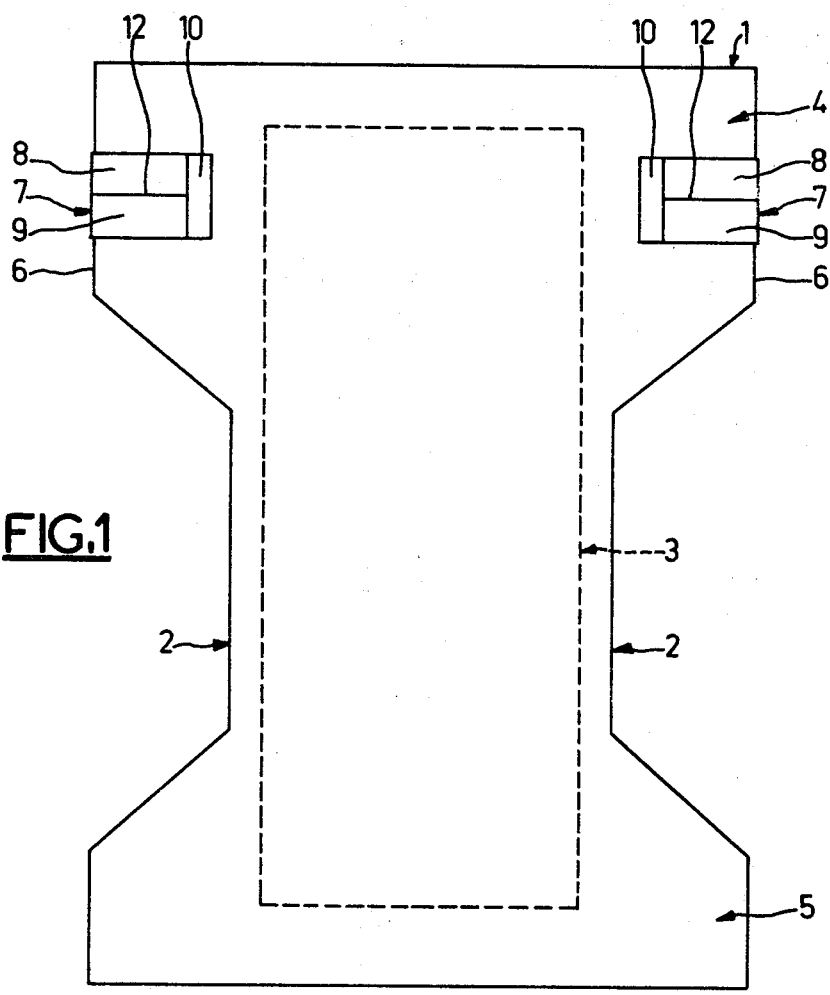
FIG. 1 is a plan view of a disposable diaper fitted with two securing devices according to the invention, with the disposable diaper being shown flat.

In FIG. 1 a diaper for infants is shown comprising an envelope or backing consisting of an impermeable, thin, flexible sheet 1, of polyethylene for example. The sheet 1, which has an overall rectangular shape, has two lateral cut-outs 2 in the crotch area for the infant's legs. On one face of the sheet 1 is absorbent padding 3 which extends on either side of the crotch area as far as the wider sections 4 and 5 of sheet 1, respectively forming the back and front of the diaper. A permeable facing web, not shown, of a non-woven fabric for example, covers the sheet 1 and the padding.

To make it possible to close the disposable diaper at the level of the infant's waist, the back part 4 of the sheet 1 has, on each lateral margin 6, an adhesive-type securing device 7. Each securing device 7 comprises two adhesive tabs 8 and 9 placed side by side and fixed to the back part 4 of the sheet 1. The two tabs 8 and 9 are turned down, before use, onto the face of the sheet 1 carrying the absorbent padding 3. At this position the sheet 1 has a piece 10 of a sheet material to which the turned-down adhesive tabs 8 and 9 adhere only moderately.

Figure 2:
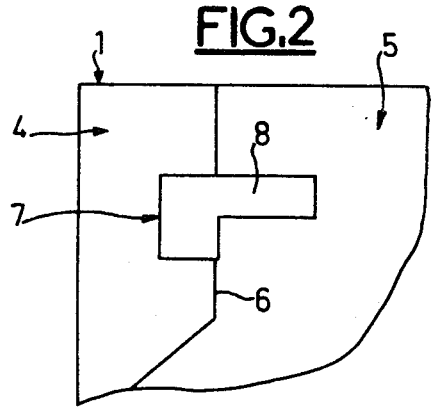
FIG. 2 is a partial view of the disposable diaper in FIG. 1 showing a securing device after the first diaper closing operation.

After the infant has been ladi onto the open diaper, the front part 5 of the sheet 1 is applied to the infant's stomach and the two sides of the back part 4 are folded over onto the two sides of the front part 5, as shown in FIG. 2. One of the two tabs, in this case tab 8, is then detached from the sheet piece 10 and is applied onto the front part 5 of the diaper, i.e. directly onto the sheet 1.

If it is required to reopen the diaper, for example to check whether the absorbent padding 3 is wet, the adhesive tab 8 is torn between the area by which it is adhered to the front part 5 and the area by which the tab 8 is fixed to the back part 4. It can be seen in FIG. 3 that the tab 8 tear line 11 runs level which the side edge 6 of the back part 4 of the diaper.

Figure 3:
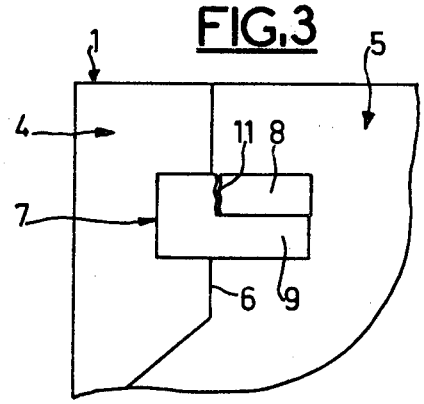
FIG. 3 is a view corresponding to the view in FIG. 2 showing the securing device after the second diaper closing operation.

In order to subsequently reclose the diaper the other adhesive tab 9 is unstuck from the sheet piece 10 and is applied onto the front part 5 of the diaper, as shown in FIG. 3.

To make it possible to tear through the tabs 8 and 9, these are made advantageously from a material which has a tear strength lower than the resistance of the adhesive tabs to ripping from the sheet 1 of the diaper, and lower than the tear strength of this same sheet 1. The adhesive tabs 8 and 9 may, for example, consist of paper or a similar frangible material which nevertheless possesses sufficient tear strength to be capable of withstanding the stresses arising from tightening the diaper round the infant's waist. It is also possible to make them from a stronger material and provide each of them with a line of least resistance facilitating tearing, or with a tear initiator.

According to a particularly advantageous embodiment of the invention, each securing device 7 is made up of a piece of adhesive tape wider than the adhesive tapes used for manufacturing normal single-adhesive-tab securing devices. This piece of adhesive tape is usually fixed over its whole width to the back part 4 of the diaper, and the part running past the side edge 6 of the back part 4 is then split along the length of the piece of adhesive tape as shown by the line 12 in FIG. 1. Thus, all that has to be done is to adjust the machines already in existence to a larger adhesive tape width and to provide a cutting station to split the section of the adhesive tape piece which extends beyond the lateral edge 6 into two.

It goes without saying that many modifications and variants can be made to the object of the invention as described above and shown in the appended drawing without, however, going outside the framework of this invention. Thus, the adhesive tabs 8 and 9, instead of being turned down onto the piece of sheet material 10 before being used, could also be each provided with a protective film capable of being pulled off to expose the adhesive material on the tabs. Furthermore, particularly when adhesive tabs fitted with a protective film are used, these tabs 8 and 9 could also be stacked on top of each other instead of being placed side by side. Finally, it would be possible to provide more than two adhesive tabs on each securing device.

We claim:

1. In a disposable diaper of the type having a substantially moisture impervious thin backing sheet having a back part and a front part, and an inner face and an outerface, and carrying on its inner face an absorbent pad assembly with a permeable web facing sheet covering said backing sheet and absorbent pad assembly, and a pair of adhesive securing devices attached to a marginal portion of the back part of said backing sheet, the improvement wherein:

said diposable diaper is adapted for multiple putting on and taking off operations, with said securing device comprising;

a first longitudinal portion fixedly attached along its entire width to the marginal portion near the lateral edge of the outer face of said back part of said backing sheet;

a second longitudinal portion integral with said first longitudinal portion, and said second longitudinal portion divided along its entire length into at least two adhesive securing tabs positioned side by side and separated by a longitudinal split line which in use extends outside said lateral edge of said backing sheet, and each of said at least two adhesive securing tabs having an adhesive coating, on the face directed toward the inner face of said backing sheet, and each adapted to be contacted and adhered to the outerface of said front part of said backing sheet to close said disposable diaper around an infant; and means for individually covering, before use, the respective adhesive coating of said at least two adhesive securing tabs, with said at least two adhesive securing tabs adapted for being respectively individually torn along a tear line running substantially along said lateral edge of the backing sheet, whereby when said diaper is first put on for wearing only one of said at least two adhesive securing tabs is adhered to the outerface of said backing sheet, and upon a subsequent opening and closing of said diaper, said one adhesive securing tab is individually torn along said tear line, and another of said at least two adhesive securing tabs is adhered to the outerface of said backing sheet.

2. The disposable diaper of claim 1, wherein said means for covering the respective adhesive coating of said at least two individual adhesive securing tabs comprises a piece of release material attached to the inner face of said back part of said backing sheet, and positioned substantially opposite to said first longitudinal portion of said at least two securing devices, and adapted for contacting the respective adhesive coating of said two individual adhesive securing tabs in a moderately adhesive manner such that each said individual adhesive securing tabs may be successively peeled off for successive attachement to the outer face of said backing sheet.

3. The disposable diaper of claim 1, wherein said means for covering the respective adhesive coatings of said at least two individual adhesive securing tabs comprises a respective plurality of protective film elements with each of said protective elements covering an adhesive coating of respective ones of said at least two adhesive securing tabs, and the material of said protective film elements being adapted for easy peeling off from said adhesive coating.

4. The disposable diaper of claim 1, wherein each of said at least two adhesive securing tabs is provided with a line of least resistance for tearing individual securing tabs substantially along said lateral edge of the backing sheet.

5. The disposable diaper of claim 1, wherein each of said at least two securing tabs is adapted for respectively individually providing sufficient adhesiveness for holding the diaper closed in the manner of single use securing devices for diapers.

6. The disposable diaper of claim 1, wherein said at least two securing tabs comprise only two securing tabs.

* * * * *